US012472331B2

(12) United States Patent
Mckinnon et al.

(10) Patent No.: US 12,472,331 B2
(45) Date of Patent: Nov. 18, 2025

(54) NEEDLE TIP BLUNTING USING A LENGTH OF A GUIDEWIRE

(71) Applicant: Bard Access Systems, Inc., Salt Lake City, UT (US)

(72) Inventors: Austin J. Mckinnon, Herriman, UT (US); Glade H. Howell, Draper, UT (US)

(73) Assignee: Bard Access Systems, Inc., Salt Lake City, UT (US)

( * ) Notice: Subject to any disclaimer, the term of this patent is extended or adjusted under 35 U.S.C. 154(b) by 946 days.

(21) Appl. No.: 17/540,988

(22) Filed: Dec. 2, 2021

(65) Prior Publication Data

US 2022/0176082 A1 Jun. 9, 2022

Related U.S. Application Data

(60) Provisional application No. 63/120,913, filed on Dec. 3, 2020.

(51) Int. Cl.
*A61M 25/09* (2006.01)
*A61M 25/00* (2006.01)

(52) U.S. Cl.
CPC ..... *A61M 25/09* (2013.01); *A61M 2025/0042* (2013.01); *A61M 2025/09083* (2013.01)

(58) Field of Classification Search
CPC .......... A61M 25/09; A61M 2025/0042; A61M 2025/0004; A61M 2210/12;
(Continued)

(56) References Cited

U.S. PATENT DOCUMENTS 1,013,691 A 1/1912 Shields
3,225,762 A 12/1965 Guttman
(Continued)

FOREIGN PATENT DOCUMENTS

CN 202526749 U 11/2012
EP 0641571 A1 3/1995
(Continued)

OTHER PUBLICATIONS

PCT/US2022/047252 filed Oct. 20, 2022 International Search Report and Written Opinion dated Mar. 21, 2023.
(Continued)

*Primary Examiner* — Laura A Bouchelle
(74) *Attorney, Agent, or Firm* — Rutan & Tucker LLP

(57) ABSTRACT

Guidewires include a distal section, a proximal section and a middle section disposed between the distal section and the proximal section, wherein the middle section has a flexural stiffness that is greater than a flexural stiffness of both of the distal section and the proximal section. The distal section is configured for insertion into a vasculature of a patient. A diameter of the middle section may be greater than a diameter of the distal section. The guidewires may include a tapered distal transition portion disposed between the distal section and the middle section and a solid core wire extending a length of the guidewires, the solid core wire including a first diameter extending along the distal section, a second diameter extending along the proximal section, and a third diameter extending along the middle section, wherein the third diameter is greater than the first diameter and second diameter.

9 Claims, 4 Drawing Sheets

(58) Field of Classification Search
CPC ........... A61M 2025/09075; A61M 2025/0915; A61M 2025/09083; A61M 2025/0175; A61M 2025/09058; A61M 2025/09133
USPC ...................................................... 604/164.13
See application file for complete search history.

(56) References Cited

U.S. PATENT DOCUMENTS

| | | | |
|---|---|---|---|
| 3,890,976 | A | 6/1975 | Bazell et al. |
| 4,051,849 | A | 10/1977 | Poncy et al. |
| 4,205,675 | A | 6/1980 | Vaillancourt |
| 4,292,970 | A | 10/1981 | Hession, Jr. |
| 4,468,224 | A | 8/1984 | Enzmann et al. |
| 4,525,157 | A | 6/1985 | Vaillancourt |
| 4,581,019 | A | 4/1986 | Curelaru et al. |
| 4,637,404 | A | 1/1987 | Gessman |
| 4,840,613 | A | 6/1989 | Balbierz |
| 4,935,008 | A | 6/1990 | Lewis, Jr. |
| 4,995,872 | A | 2/1991 | Ferrara |
| 5,017,259 | A | 5/1991 | Kohsai |
| 5,040,548 | A | 8/1991 | Yock |
| 5,057,073 | A | 10/1991 | Martin |
| 5,112,312 | A | 5/1992 | Luther |
| 5,120,317 | A | 6/1992 | Luther |
| 5,188,593 | A | 2/1993 | Martin |
| 5,195,962 | A | 3/1993 | Martin et al. |
| 5,207,650 | A | 5/1993 | Martin |
| 5,263,938 | A | 11/1993 | Orr et al. |
| 5,267,958 | A | 12/1993 | Buchbinder et al. |
| 5,273,042 | A | 12/1993 | Lynch et al. |
| 5,282,479 | A | 2/1994 | Havran |
| 5,295,970 | A | 3/1994 | Clinton et al. |
| 5,306,247 | A | 4/1994 | Pfenninger |
| 5,328,472 | A | 7/1994 | Steinke et al. |
| 5,350,358 | A | 9/1994 | Martin |
| 5,363,847 | A | 11/1994 | Viera |
| 5,368,567 | A | 11/1994 | Lee |
| 5,378,230 | A | 1/1995 | Mahurkar |
| 5,380,290 | A | 1/1995 | Makower et al. |
| 5,380,307 | A * | 1/1995 | Chee ................. A61M 25/0054 604/266 |
| 5,389,087 | A | 2/1995 | Miraki |
| 5,420,882 | A | 5/1995 | Black |
| 5,439,449 | A | 8/1995 | Mapes et al. |
| 5,443,457 | A | 8/1995 | Ginn et al. |
| 5,489,271 | A | 2/1996 | Andersen |
| 5,573,520 | A | 11/1996 | Schwartz et al. |
| 5,683,370 | A | 11/1997 | Luther et al. |
| 5,718,678 | A | 2/1998 | Fleming, III |
| 5,772,636 | A | 6/1998 | Brimhall et al. |
| 5,827,202 | A | 10/1998 | Miraki et al. |
| 5,885,251 | A | 3/1999 | Luther |
| 5,919,164 | A | 7/1999 | Andersen |
| 5,947,940 | A | 9/1999 | Beisel |
| 5,957,893 | A | 9/1999 | Luther et al. |
| 6,123,084 | A | 9/2000 | Jandak et al. |
| 6,206,849 | B1 | 3/2001 | Martin et al. |
| 6,228,062 | B1 | 5/2001 | Howell et al. |
| 6,475,187 | B1 | 11/2002 | Gerberding |
| 6,606,515 | B1 | 8/2003 | Windheuser et al. |
| 6,716,228 | B2 | 4/2004 | Tal |
| 6,726,659 | B1 | 4/2004 | Stocking et al. |
| 6,819,951 | B2 | 11/2004 | Patel et al. |
| 6,821,287 | B1 | 11/2004 | Jang |
| 6,926,692 | B2 | 8/2005 | Katoh et al. |
| 6,962,575 | B2 | 11/2005 | Tal |
| 6,994,693 | B2 | 2/2006 | Tal |
| 6,999,809 | B2 | 2/2006 | Currier et al. |
| 7,025,746 | B2 | 4/2006 | Tal |
| 7,029,467 | B2 | 4/2006 | Currier et al. |
| 7,037,293 | B2 | 5/2006 | Carrillo et al. |
| 7,074,231 | B2 | 7/2006 | Jang |
| 7,141,050 | B2 | 11/2006 | Deal et al. |
| 7,144,386 | B2 | 12/2006 | Korkor et al. |
| 7,311,697 | B2 | 12/2007 | Osborne |
| 7,364,566 | B2 | 4/2008 | Elkins et al. |
| 7,377,910 | B2 | 5/2008 | Katoh et al. |
| 7,390,323 | B2 | 6/2008 | Jang |
| D600,793 | S | 9/2009 | Bierman et al. |
| D601,242 | S | 9/2009 | Bierman et al. |
| D601,243 | S | 9/2009 | Bierman et al. |
| 7,594,911 | B2 | 9/2009 | Powers et al. |
| 7,691,093 | B2 | 4/2010 | Brimhall |
| 7,722,567 | B2 | 5/2010 | Tal |
| D617,893 | S | 6/2010 | Bierman et al. |
| D624,643 | S | 9/2010 | Bierman et al. |
| 7,819,889 | B2 | 10/2010 | Healy et al. |
| 7,857,770 | B2 | 12/2010 | Raulerson et al. |
| 7,857,788 | B2 | 12/2010 | Racz |
| D630,729 | S | 1/2011 | Bierman et al. |
| 7,909,797 | B2 | 3/2011 | Kennedy, II et al. |
| 7,909,811 | B2 | 3/2011 | Agro et al. |
| 7,922,696 | B2 | 4/2011 | Tal et al. |
| 7,938,820 | B2 | 5/2011 | Webster et al. |
| 7,967,834 | B2 | 6/2011 | Tal et al. |
| 7,985,204 | B2 | 7/2011 | Katoh et al. |
| 8,073,517 | B1 | 12/2011 | Burchman |
| 8,105,286 | B2 | 1/2012 | Anderson et al. |
| 8,192,402 | B2 | 6/2012 | Anderson et al. |
| 8,202,251 | B2 | 6/2012 | Bierman et al. |
| 8,206,356 | B2 | 6/2012 | Katoh et al. |
| 8,372,107 | B2 | 2/2013 | Tupper |
| 8,377,006 | B2 | 2/2013 | Tal et al. |
| 8,454,577 | B2 | 6/2013 | Joergensen et al. |
| 8,585,858 | B2 | 11/2013 | Kronfeld et al. |
| 8,652,119 | B2 | 2/2014 | Nishigishi |
| 8,657,790 | B2 | 2/2014 | Tal et al. |
| 8,672,888 | B2 | 3/2014 | Tal |
| 8,696,645 | B2 | 4/2014 | Tal et al. |
| 8,784,362 | B2 | 7/2014 | Boutilette et al. |
| 8,827,958 | B2 | 9/2014 | Bierman et al. |
| 8,876,704 | B2 | 11/2014 | Golden et al. |
| 8,882,713 | B1 | 11/2014 | Call et al. |
| 8,900,192 | B2 | 12/2014 | Anderson et al. |
| 8,900,207 | B2 | 12/2014 | Uretsky |
| 8,915,884 | B2 | 12/2014 | Tal et al. |
| 8,956,327 | B2 | 2/2015 | Bierman et al. |
| 9,023,093 | B2 | 5/2015 | Pal |
| 9,138,252 | B2 | 9/2015 | Bierman et al. |
| 9,180,275 | B2 | 11/2015 | Helm |
| 9,265,920 | B2 | 2/2016 | Rundquist et al. |
| 9,272,121 | B2 | 3/2016 | Piccagli |
| 9,522,254 | B2 | 12/2016 | Belson |
| 9,554,785 | B2 | 1/2017 | Walters et al. |
| 9,566,087 | B2 | 2/2017 | Bierman et al. |
| 9,579,484 | B2 | 2/2017 | Barnell |
| 9,675,784 | B2 | 6/2017 | Belson |
| 9,713,695 | B2 | 7/2017 | Bunch et al. |
| 9,764,117 | B2 | 9/2017 | Bierman et al. |
| 9,770,573 | B2 | 9/2017 | Golden et al. |
| 9,814,861 | B2 | 11/2017 | Boutillette et al. |
| 9,820,845 | B2 | 11/2017 | von Lehe et al. |
| 9,861,383 | B2 | 1/2018 | Clark |
| 9,884,169 | B2 | 2/2018 | Bierman et al. |
| 9,889,275 | B2 | 2/2018 | Voss et al. |
| 9,913,585 | B2 | 3/2018 | McCaffrey et al. |
| 9,913,962 | B2 | 3/2018 | Tal et al. |
| 9,981,113 | B2 | 5/2018 | Bierman |
| 10,010,312 | B2 | 7/2018 | Tegels |
| 10,065,020 | B2 | 9/2018 | Gaur |
| 10,098,724 | B2 | 10/2018 | Adams et al. |
| 10,111,683 | B2 | 10/2018 | Tsamir et al. |
| 10,118,020 | B2 | 11/2018 | Avneri et al. |
| 10,130,269 | B2 | 11/2018 | McCaffrey et al. |
| 10,220,184 | B2 | 3/2019 | Clark |
| 10,220,191 | B2 | 3/2019 | Belson et al. |
| 10,265,508 | B2 | 4/2019 | Baid |
| 10,271,873 | B2 | 4/2019 | Steingisser et al. |
| 10,376,675 | B2 | 8/2019 | Mitchell et al. |
| 10,675,440 | B2 | 6/2020 | Abitabilo et al. |
| 10,806,901 | B2 | 10/2020 | Burkholz et al. |
| 11,285,301 | B2 | 3/2022 | Ornelas Vargas et al. |
| 2002/0040231 | A1 | 4/2002 | Wysoki |
| 2002/0198492 | A1 | 12/2002 | Miller et al. |

(56) References Cited

U.S. PATENT DOCUMENTS

2003/0036712 A1 2/2003 Heh et al.
2003/0060863 A1 3/2003 Dobak
2003/0088212 A1 5/2003 Tal
2003/0100849 A1 5/2003 Jang
2003/0153874 A1 8/2003 Tal
2003/0158514 A1 8/2003 Tal
2004/0116901 A1 6/2004 Appling
2004/0193093 A1 9/2004 Desmond
2004/0225232 A1* 11/2004 Malmborg ........... A61B 5/0215 600/585
2004/0230178 A1 11/2004 Wu
2005/0004554 A1 1/2005 Osborne
2005/0245847 A1 11/2005 Schaeffer
2005/0245882 A1 11/2005 Elkins et al.
2005/0283221 A1 12/2005 Mann et al.
2006/0009740 A1 1/2006 Higgins et al.
2006/0064036 A1* 3/2006 Osborne ............... A61M 25/09 600/585
2006/0116629 A1 6/2006 Tal et al.
2006/0129100 A1 6/2006 Tal
2006/0129130 A1 6/2006 Tal et al.
2007/0276288 A1 11/2007 Khaw
2008/0045894 A1 2/2008 Perchik et al.
2008/0058839 A1* 3/2008 Nobles .................. A61M 25/09 128/898
2008/0091137 A1 4/2008 Reavill
2008/0125744 A1 5/2008 Treacy
2008/0125748 A1 5/2008 Patel
2008/0262430 A1 10/2008 Anderson et al.
2008/0262431 A1 10/2008 Anderson et al.
2008/0294111 A1 11/2008 Tal et al.
2008/0312578 A1 12/2008 DeFonzo et al.
2009/0105653 A1 4/2009 Spenser et al.
2009/0221961 A1 9/2009 Tal et al.
2009/0227900 A1 9/2009 Kim et al.
2009/0270889 A1 10/2009 Tal et al.
2010/0256487 A1 10/2010 Hawkins et al.
2010/0305474 A1 12/2010 DeMars et al.
2011/0004162 A1 1/2011 Tal
2011/0009827 A1 1/2011 Bierman et al.
2011/0021994 A1 1/2011 Anderson et al.
2011/0066142 A1 3/2011 Tal et al.
2011/0106057 A1 5/2011 Hamboly
2011/0144620 A1 6/2011 Tal
2011/0152836 A1 6/2011 Riopelle et al.
2011/0202006 A1 8/2011 Bierman et al.
2011/0251559 A1 10/2011 Tal et al.
2011/0270192 A1 11/2011 Anderson et al.
2012/0004665 A1 1/2012 Defossez et al.
2012/0041371 A1 2/2012 Tal et al.
2012/0065590 A1 3/2012 Bierman et al.
2012/0071857 A1 3/2012 Goldfarb et al.
2012/0078231 A1 3/2012 Hoshinouchi
2012/0130411 A1 5/2012 Tal et al.
2012/0130415 A1 5/2012 Tal et al.
2012/0157854 A1 6/2012 Kurrus et al.
2012/0220942 A1 8/2012 Hall et al.
2012/0283640 A1 11/2012 Anderson et al.
2012/0316500 A1 12/2012 Bierman et al.
2013/0053826 A1 2/2013 Shevgoor
2013/0123704 A1 5/2013 Bierman et al.
2013/0158338 A1 6/2013 Kelly et al.
2013/0188291 A1 7/2013 Vardiman
2013/0237931 A1 9/2013 Tal et al.
2013/0304030 A1* 11/2013 Gray ..................... A61M 25/09 604/528
2013/0306079 A1 11/2013 Tracy
2014/0025036 A1 1/2014 Bierman et al.
2014/0081210 A1 3/2014 Bierman et al.
2014/0100552 A1 4/2014 Gallacher et al.
2014/0207052 A1 7/2014 Tal et al.
2014/0207069 A1 7/2014 Bierman et al.
2014/0214005 A1 7/2014 Belson
2014/0257111 A1 9/2014 Yamashita et al.
2014/0276432 A1 9/2014 Bierman et al.
2014/0276599 A1 9/2014 Cully et al.
2015/0045695 A1 2/2015 Simpson et al.
2015/0080939 A1 3/2015 Adams et al.
2015/0112310 A1 4/2015 Call et al.
2015/0126930 A1 5/2015 Bierman et al.
2015/0148595 A1 5/2015 Bagwell et al.
2015/0190168 A1 7/2015 Bierman et al.
2015/0196210 A1 7/2015 McCaffrey et al.
2015/0224287 A1 8/2015 Bian et al.
2015/0231364 A1 8/2015 Blanchard et al.
2015/0283357 A1 10/2015 Lampropoulos et al.
2015/0290432 A1 10/2015 Mathews et al.
2015/0297867 A1 10/2015 Howell et al.
2015/0297868 A1 10/2015 Tal et al.
2015/0320969 A1 11/2015 Haslinger et al.
2015/0328434 A1* 11/2015 Gaur ................. A61M 25/0026 604/510
2015/0351793 A1 12/2015 Bierman et al.
2015/0359549 A1 12/2015 Lenker et al.
2015/0359998 A1 12/2015 Carmel et al.
2016/0074628 A1 3/2016 Smith et al.
2016/0082223 A1 3/2016 Barnell
2016/0114124 A1 4/2016 Tal
2016/0220786 A1 8/2016 Mitchell et al.
2016/0325073 A1 11/2016 Davies et al.
2016/0338728 A1 11/2016 Tal
2016/0346503 A1 12/2016 Jackson et al.
2017/0014599 A1 1/2017 Crisman et al.
2017/0035990 A1 2/2017 Swift
2017/0072165 A1 3/2017 Lim et al.
2017/0080189 A1 3/2017 Tao et al.
2017/0128700 A1 5/2017 Roche Rebollo
2017/0172653 A1 6/2017 Urbanski et al.
2017/0239443 A1 8/2017 Abitabilo et al.
2017/0273713 A1 9/2017 Shah et al.
2017/0296792 A1 10/2017 Ornelas Vargas et al.
2017/0326339 A1 11/2017 Bailey et al.
2017/0361070 A1 12/2017 Hivert
2018/0021545 A1 1/2018 Mitchell et al.
2018/0116690 A1 5/2018 Sarabia et al.
2018/0117284 A1 5/2018 Appling et al.
2018/0133438 A1 5/2018 Hulvershorn et al.
2018/0154062 A1 6/2018 DeFonzo et al.
2018/0154112 A1 6/2018 Chan et al.
2018/0296799 A1 10/2018 Horst et al.
2018/0296804 A1 10/2018 Bierman
2019/0015646 A1 1/2019 Matlock et al.
2019/0046770 A1 2/2019 Shields
2019/0060616 A1 2/2019 Solomon
2019/0076167 A1 3/2019 Fantuzzi et al.
2019/0134349 A1 5/2019 Cohn et al.
2019/0255294 A1 8/2019 Mitchell et al.
2019/0276268 A1 9/2019 Akingba
2019/0321590 A1 10/2019 Burkholz et al.
2020/0016374 A1 1/2020 Burkholz et al.
2021/0069471 A1 3/2021 Howell
2021/0085927 A1 3/2021 Howell
2021/0121661 A1 4/2021 Howell
2021/0121667 A1 4/2021 Howell
2021/0228843 A1 7/2021 Howell et al.
2021/0307854 A1 10/2021 Bernhard et al.
2021/0322729 A1 10/2021 Howell
2021/0330941 A1 10/2021 Howell et al.
2021/0330942 A1 10/2021 Howell
2021/0361915 A1 11/2021 Howell et al.
2021/0402149 A1 12/2021 Howell
2021/0402153 A1 12/2021 Howell et al.
2022/0001138 A1 1/2022 Howell
2022/0032013 A1 2/2022 Howell et al.
2022/0047267 A1* 2/2022 Johnston ............. A61M 1/3655
2022/0193379 A1 6/2022 Howell
2022/0409275 A1 12/2022 Hoang et al.
2023/0128853 A1 4/2023 Lindekugel et al.

(56) References Cited

U.S. PATENT DOCUMENTS

| | | | |
|---|---|---|---|
| 2023/0129318 | A1 | 4/2023 | Lindekugel et al. |
| 2023/0277812 | A1 | 9/2023 | Howell et al. |

FOREIGN PATENT DOCUMENTS

| | | | |
|---|---|---|---|
| EP | 0730880 | A1 | 9/1996 |
| EP | 2061385 | A1 | 5/2009 |
| EP | 1458437 | B1 | 3/2010 |
| EP | 2248549 | A2 | 11/2010 |
| EP | 2319576 | A1 | 5/2011 |
| EP | 2366422 | A1 | 9/2011 |
| EP | 2433670 | A1 | 3/2012 |
| EP | 2486880 | A2 | 8/2012 |
| EP | 2486881 | A2 | 8/2012 |
| EP | 2486951 | A2 | 8/2012 |
| EP | 2512576 | A2 | 10/2012 |
| EP | 2152348 | B1 | 2/2015 |
| EP | 3205368 | A1 | 8/2017 |
| EP | 3093038 | B1 | 5/2019 |
| EP | 2260897 | B1 | 9/2019 |
| GB | 1273547 | A | 5/1972 |
| WO | 9306878 | A1 | 4/1993 |
| WO | 94/21315 | A1 | 9/1994 |
| WO | 95/32009 | A2 | 11/1995 |
| WO | 98/44979 | A1 | 10/1998 |
| WO | 98/53871 | A1 | 12/1998 |
| WO | 99/12600 | A1 | 3/1999 |
| WO | 99/26681 | A1 | 6/1999 |
| WO | 02/05886 | A1 | 1/2002 |
| WO | 2003008020 | A1 | 1/2003 |
| WO | 2003057272 | A2 | 7/2003 |
| WO | 2003066125 | A2 | 8/2003 |
| WO | 2006055288 | A2 | 5/2006 |
| WO | 2006055780 | A2 | 5/2006 |
| WO | 2006/096262 | A2 | 9/2006 |
| WO | 2007046850 | A2 | 4/2007 |
| WO | 2008005618 | A2 | 1/2008 |
| WO | 2008033983 | A1 | 3/2008 |
| WO | 2008092029 | A2 | 7/2008 |
| WO | 2008/107869 | A1 | 9/2008 |
| WO | 2008/131300 | A2 | 10/2008 |
| WO | 2008131289 | A2 | 10/2008 |
| WO | 2008133808 | A1 | 11/2008 |
| WO | 2009114833 | A1 | 9/2009 |
| WO | 2009114837 | A2 | 9/2009 |
| WO | 2010/048449 | A2 | 4/2010 |
| WO | 2010056906 | A2 | 5/2010 |
| WO | 2010083467 | A2 | 7/2010 |
| WO | 2010/132608 | A2 | 11/2010 |
| WO | 2011081859 | A2 | 7/2011 |
| WO | 2011097639 | A2 | 8/2011 |
| WO | 2011146764 | A1 | 11/2011 |
| WO | 2012068162 | A2 | 5/2012 |
| WO | 2012068166 | A2 | 5/2012 |
| WO | 2012135761 | A1 | 10/2012 |
| WO | 2012162677 | A1 | 11/2012 |
| WO | 2013026045 | A1 | 2/2013 |
| WO | 2013138519 | A1 | 9/2013 |
| WO | 2014006403 | A1 | 1/2014 |
| WO | 2014/100392 | A1 | 6/2014 |
| WO | 2014113257 | A2 | 7/2014 |
| WO | 2014152005 | A2 | 9/2014 |
| WO | 2014197614 | A2 | 12/2014 |
| WO | 2015057766 | A1 | 4/2015 |
| WO | 2016110824 | A1 | 7/2016 |
| WO | 2016123278 | A1 | 8/2016 |
| WO | 2016139590 | A1 | 9/2016 |
| WO | 2016139597 | A2 | 9/2016 |
| WO | 2016176065 | A1 | 11/2016 |
| WO | 2018089275 | A1 | 5/2018 |
| WO | 2018089285 | A1 | 5/2018 |
| WO | 2018089385 | A1 | 5/2018 |
| WO | 2018191547 | A1 | 10/2018 |
| WO | 2018213148 | A1 | 11/2018 |
| WO | 2018218236 | A1 | 11/2018 |
| WO | 2019/146026 | A1 | 8/2019 |
| WO | 2019199734 | A1 | 10/2019 |
| WO | 2020069395 | A1 | 4/2020 |
| WO | 2021050302 | A1 | 3/2021 |
| WO | 2021/077103 | A1 | 4/2021 |
| WO | 2021062023 | A1 | 4/2021 |
| WO | 2021081205 | A1 | 4/2021 |
| WO | 2021086793 | A1 | 5/2021 |
| WO | 2022/120068 | A1 | 6/2022 |
| WO | 2022/133138 | A2 | 6/2022 |
| WO | 2023069600 | A1 | 4/2023 |
| WO | 2023069726 | A1 | 4/2023 |
| WO | 2023167940 | A1 | 9/2023 |

OTHER PUBLICATIONS

PCT/US2022/047444 filed Oct. 21, 2022 International Search Report and Written Opinion dated Mar. 7, 2023.

U.S. Appl. No. 17/079,320, filed Oct. 23, 2020 Restriction Requirement dated Mar. 29, 2023.

PCT/US2020/057202 filed Oct. 23, 2020 International Preliminary Report on Patentability dated Apr. 26, 2022.

PCT/US2020/057202 filed Oct. 23, 2020 International Search Report and Written Opinion dated Jan. 21, 2021.

PCT/US2021/022208 filed Mar. 12, 2021 International Search Report and Written Opinion dated Sep. 3, 2021.

PCT/US2021/022226 filed Mar. 12, 2021 International Search Report and Written Opinion dated Oct. 21, 2021.

PCT/US2021/061638 filed Dec. 2, 2021 International Search Report and Written Opinion dated Apr. 12, 2022.

U.S. Appl. No. 17/079,320, filed Oct. 23, 2020 Notice of Allowance dated Aug. 20, 2024.

U.S. Appl. No. 17/200,630, filed Mar. 12, 2021 Non-Final Office Action dated Jun. 4, 2024.

U.S. Appl. No. 17/200,630, filed Mar. 12, 2021 Notice of Allowance dated Sep. 11, 2024.

U.S. Appl. No. 17/553,609, filed Dec. 16, 2021 Non-Final Office Action dated Oct. 15, 2024.

PCT/US2023/014295 filed Mar. 1, 2023 International Search Report and Written Opinion dated Jun. 23, 2023.

U.S. Appl. No. 17/079,320, filed Oct. 23, 2020 Non-Final Office Action dated Jul. 28, 2023.

U.S. Appl. No. 17/200,566, filed Mar. 12, 2021 Restriction Requirement dated Jul. 14, 2023.

PCT/US2021/063903 filed Dec. 16, 2021, International Search Report and Written Opinion dated Jun. 28, 2022.

Strittmatter, F., Eisel, M., Brinkmann, R., Cordes, J., Lange, B., & Sroka, R., "Laser Induced Lithotripsy: a Review, insight into laboratory work, and lessons learned." Translational Biophotonics, 2(1-2), e201900029. (2020).

Traxer, O., & Keller, E. X., "Thulium fiber laser: the new player for kidney stone treatment? A comparison with Holmium: YAG laser." World Journal of Urology, 38, 1883-1894. (2020).

U.S. Appl. No. 17/079,320, filed Oct. 23, 2020 Advisory Action dated Apr. 11, 2024.

U.S. Appl. No. 17/079,320, filed Oct. 23, 2020 Final Office Action dated Jan. 18, 2024.

U.S. Appl. No. 17/079,320, filed Oct. 23, 2020 Non-Final Office Action dated May 7, 2024.

U.S. Appl. No. 17/200,566, filed Mar. 12, 2021 Final Office Action dated Dec. 28, 2023.

U.S. Appl. No. 17/200,566, filed Mar. 12, 2021 Notice of Allowance dated Apr. 3, 2024.

U.S. Appl. No. 17/200,630, filed Mar. 12, 2021 Advisory Action dated May 10, 2024.

U.S. Appl. No. 17/200,630, filed Mar. 12, 2021 Final Office Action dated Feb. 5, 2024.

U.S. Appl. No. 17/200,566, filed Mar. 12, 2021 Non-Final Office Action dated Oct. 6, 2023.

U.S. Appl. No. 17/200,630, filed Mar. 12, 2021 Non-Final Office Action dated Sep. 27, 2023.

(56) References Cited

OTHER PUBLICATIONS

U.S. Appl. No. 17/200,630, filed Mar. 12, 2021 Restriction Requirement dated Jul. 14, 2023.

* cited by examiner

NEEDLE TIP BLUNTING USING A LENGTH OF A GUIDEWIRE

PRIORITY

This application claims the benefit of priority to U.S. Provisional Application No. 63/120,913, filed Dec. 3, 2020, which is incorporated by reference in its entirety into this application.

BACKGROUND

The insertion of intravascular catheters through the skin and into the vasculature of a patient generally includes the use of a needle disposed within the lumen of the catheter. The needle provides a sharp tip and adds stiffness to the catheter to aid the insertion process. Catheters may come packaged with a needle already inserted or the clinician may insert the needle into the catheter at the point of use. In some instances, a clinician may reinsert a needle into a catheter after initial placement of the catheter. The rapid placement of larger catheters such a central venous catheters (CVC) may include inserting an introducer catheter through a lumen of the CVC. In such an instance, the introducer catheter may comprise a needle. The forgoing are just a few examples of many situations where a clinician may insert a needle through a catheter lumen. The tubular portions of the catheters are flexible and may be several inches in length. These characteristics pose difficulty when inserting a sharp needle through the lumen of the catheter. The insertion of the needle though the lumen of the catheter can also potentially pierce the catheter's tubular wall rendering the catheter unfit for use. As set forth above, there is a need to reduce the propensity of the needle tip to puncture a catheter wall upon insertion of the needle through the lumen of the catheter lumen. Disclosed herein are needle tip blunting guidewires and methods thereof that address the foregoing.

SUMMARY

Disclosed herein are embodiments of a guidewire, including a flexible distal section, flexible proximal section, and a middle section disposed between the distal section and the proximal section. In some embodiments, the distal section is configured for insertion into a vasculature of a patient. In some embodiments, the middle section is less flexible than the distal section and the proximal section. The middle section may be stiff and a diameter of the middle section may be greater than a diameter of the distal section. In some embodiments, a tapered distal transition portion is disposed between the distal section and the middle section.

In some embodiments, the guidewire comprises a solid core wire extending a length of the guidewire. The solid core wire includes a first diameter extending along the distal section, a second diameter extending along the proximal section, and a third diameter extending along the middle section. The third diameter, which may be greater than the first diameter and the second diameter, defines an outside diameter of the guidewire along the middle section.

In some embodiments, the guidewire comprises a solid core wire extending a length of the guidewire and a coil disposed around the solid core wire along the length of the guidewire. The guidewire may further include a material applied around the guidewire along the middle section. The material may be a liquid during application and may transform into a solid after application.

In some embodiments, the guidewire comprises a solid core wire extending a length of the guidewire and a cannula threaded onto the solid core wire. The cannula is positioned along the middle section, and the cannula defines an outside diameter of the guidewire along the middle section.

In some embodiments, the guidewire comprises a flexible distal section, flexible proximal section, a stiff middle section disposed between the distal section and the proximal section; and a cannula threaded onto the guidewire. A distal tip of the cannula is positioned so that a proximal portion of the middle section is disposed within the cannula and a distal portion of the middle section extends distally beyond the distal tip of the cannula. An outside diameter of the middle section and an inside diameter of the cannula can: 1) define a longitudinal sliding fit between the middle section and the cannula, and 2) constrain the middle section to be parallel to the cannula.

In some embodiments, a method of using a guidewire comprises obtaining a guidewire including a flexible distal section, a flexible proximal section, and a stiff middle section disposed between the distal section and the proximal section; threading a cannula onto the guidewire; positioning a tip of the cannula between a distal end and a proximal end of the middle section; and inserting the cannula and the guidewire distally through a tubular member while maintaining the position of the cannula with respect to the guidewire. The method may further comprise contacting the tubular member with the middle section to constrain the tubular member away from a sharp point of the cannula.

In some embodiments, at least a portion of the proximal section may be disposed within the cannula after positioning the tip of the cannula between the distal end and the proximal end of the middle section. In some embodiments, the tubular member is a first intravascular catheter which may be at least partially inserted into a vasculature of a patient. In some embodiments, the method comprises inserting the guidewire and the cannula into a second intravascular catheter. In still other embodiments, the method comprises inserting the guidewire, the cannula, and the first intravascular catheter into a second intravascular catheter. In some embodiments, the method further comprises inserting the distal section of the guidewire into a vasculature and in some embodiments, the distal section is inserted into the vasculature before the cannula is threaded onto the guidewire.

These and other features of the concepts provided herein will become more apparent to those of skill in the art in view of the accompanying drawings and following description, which describe particular embodiments of such concepts in greater detail.

DRAWINGS

DESCRIPTION

Figure 1:
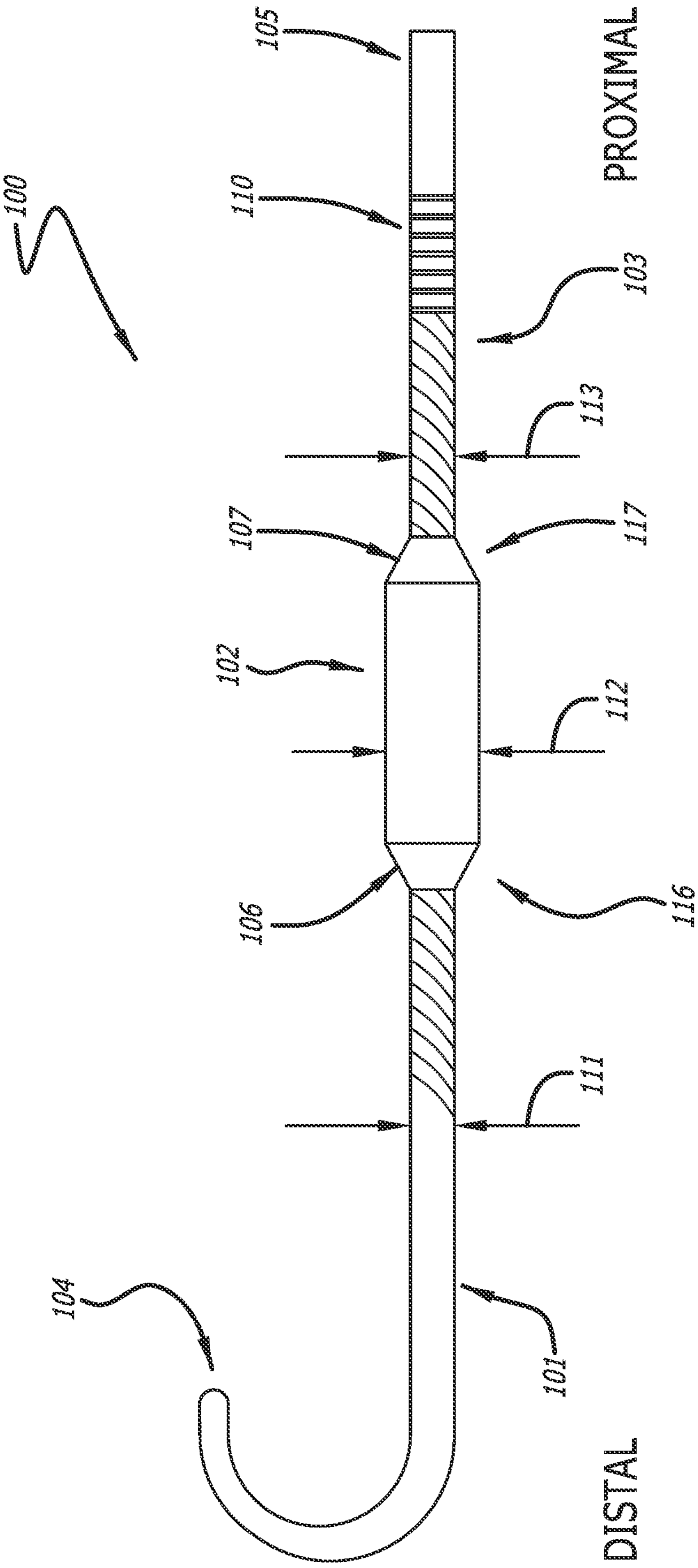
FIG. 1 illustrates a needle tip blunting guidewire, in accordance with some embodiments.

Before some particular embodiments are disclosed in greater detail, it should be understood that the particular embodiments disclosed herein do not limit the scope of the concepts provided herein. It should also be understood that a particular embodiment disclosed herein can have features that can be readily separated from the particular embodiment and optionally combined with or substituted for features of any of a number of other embodiments disclosed herein.

Regarding terms used herein, it should also be understood the terms are for the purpose of describing some particular embodiments, and the terms do not limit the scope of the concepts provided herein. Ordinal numbers (e.g., first, second, third, etc.) are generally used to distinguish or identify different features or steps in a group of features or steps, and do not supply a serial or numerical limitation. For example, "first," "second," and "third" features or steps need not necessarily appear in that order, and the particular embodiments including such features or steps need not necessarily be limited to the three features or steps. Labels such as "left," "right," "top," "bottom," "front," "back," and the like are used for convenience and are not intended to imply, for example, any particular fixed location, orientation, or direction. Instead, such labels are used to reflect, for example, relative location, orientation, or directions. Singular forms of "a," "an," and "the" include plural references unless the context clearly dictates otherwise.

With respect to "proximal," a "proximal portion" or a "proximal end portion" of, for example, a catheter disclosed herein includes a portion of the catheter intended to be near a clinician when the catheter is used on a patient. Likewise, a "proximal length" of, for example, the catheter includes a length of the catheter intended to be near the clinician when the catheter is used on the patient. A "proximal end" of, for example, the catheter includes an end of the catheter intended to be near the clinician when the catheter is used on the patient. The proximal portion, the proximal end portion, or the proximal length of the catheter can include the proximal end of the catheter; however, the proximal portion, the proximal end portion, or the proximal length of the catheter need not include the proximal end of the catheter. That is, unless context suggests otherwise, the proximal portion, the proximal end portion, or the proximal length of the catheter is not a terminal portion or terminal length of the catheter.

With respect to "distal," a "distal portion" or a "distal end portion" of, for example, a catheter disclosed herein includes a portion of the catheter intended to be near or in a patient when the catheter is used on the patient. Likewise, a "distal length" of, for example, the catheter includes a length of the catheter intended to be near or in the patient when the catheter is used on the patient. A "distal end" of, for example, the catheter includes an end of the catheter intended to be near or in the patient when the catheter is used on the patient. The distal portion, the distal end portion, or the distal length of the catheter can include the distal end of the catheter; however, the distal portion, the distal end portion, or the distal length of the catheter need not include the distal end of the catheter. That is, unless context suggests otherwise, the distal portion, the distal end portion, or the distal length of the catheter is not a terminal portion or terminal length of the catheter.

Unless defined otherwise, all technical and scientific terms used herein have the same meaning as commonly understood by those of ordinary skill in the art.

Any methods disclosed herein include one or more steps or actions for performing the described method. The method steps and/or actions may be interchanged with one another. In other words, unless a specific order of steps or actions is required for proper operation of the embodiment, the order and/or use of specific steps and/or actions may be modified. Moreover, sub-routines or only a portion of a method described herein may be a separate method within the scope of this disclosure. Stated otherwise, some methods may include only a portion of the steps described in a more detailed method.

FIG. 1 illustrates a needle tip blunting guidewire (NTBG) 100, in accordance with some embodiments described herein. The NTBG 100 may be used in conjunction with a needle cannula to blunt a sharp tip of the cannula as described in detail below. The NTBG 100 may be configured to be inserted through a cannula. The NTBG 100 includes a distal section 101, a middle section 102, a proximal section 103, a distal end 104, and a proximal end 105. Each of the sections 101, 102, and 103 may include different dimensions and properties as further described. The middle section 102 includes a distal end 116 and a proximal end 117.

The distal section 101 may be configured to be disposed within a vasculature of a patient. As such, the distal section 101 may comprise a flexibility sufficient to traverse a vasculature without causing injury to the vascular wall. In other words, the distal section 101 may flex during insertion to conform with the vasculature structure without kinking or plastically deforming. In some embodiments, the distal section 101 may comprise a flexibility that is consistent with medical guidewires configured to traverse a vasculature, as discussed further below. The distal section 101 may also comprise sufficient stiffness to facilitate insertion via a distally applied compression force without buckling within the vasculature. In some embodiments, the distal section 101 may include a length sufficient to extend from the vasculature insertion site to a desired location within the vasculature such as a location near or within the heart. As such, placement of intravascular devices may include use of the NTBG 100 as an intravascular guidewire. In other embodiments, the distal section 101 may be short, such that the distal section extends less than about 1 to 5 centimeters away from a cannula tip, for example.

The distal section 101 may comprise a round cross section having a diameter 111 consistent with insertion through the vasculature, a cannula and/or a catheter lumen. In some embodiments, the distal section 101 may comprise one or multiple preformed curves or shapes to aid insertion through the vasculature. Preformed shapes may be two-dimensional, such as the "J" shape illustrated in FIG. 1, or three-dimensional.

The proximal section 103 may be configured to be manually inserted into a cannula of a needle. The proximal section 103 may comprise adequate stiffness to facilitate being manually grasped by a clinician and urged distally into the cannula without kinking or plastically deforming. The proximal section 103 may comprise a flexibility consistent with being coiled for placement in a package container without kinking or plastically deforming. In some embodiments, the proximal section 103 may be less flexible than the distal section 101. The proximal section 103 may comprise a round cross section having a diameter 113 consistent with disposition within the cannula. In some embodiments, the diameter 113 may be larger than the diameter 111. In some embodiments, the proximal section 103 may be configured to be disposed within the vasculature of a patient and therefore, the proximal section 103 may comprise similar physical properties as the distal section 101.

In some embodiments, the proximal section 103 may include indicia 110. The indicia 110 may be indicative of a distance to the middle section 102. In some instances, the distal tip of the cannula may not be visible to a clinician. A location of indicia 110 with respect to a proximal end of the cannula may indicate a position of the middle section 102 with respect to a distal tip of the cannula. The indicia 110 may also be indicative of a distance to the distal end 104 of the NTBG 100. In some instances, a clinician may observe the indicia 110 to determine the position of the distal end 104 along the vasculature of the patient.

The middle section 102 is disposed between the distal section 101 and the proximal section 103. In the illustrated embodiment, the middle section 102 may be straight to correspond with a straight cannula. In some embodiments, the middle section 102 may comprise a curve to correspond with a curved cannula. The middle section 102 may remain straight during use. As is known, catheters, guidewires and other elongated medical devices have varying levels or degrees of stiffness (or flexibility), which is often referred to as flexural stiffness or flexural rigidity. Flexural stiffness is understood as the product of the elastic modulus (E) of a material and the area moment of inertia (I) where the flexural stiffness (EI) has the SI units of Newtons (N)·meters$^2$ ($m^2$) or N·$m^2$.

In certain situations, a particular medical procedure may require a medical device have a particular degree of stiffness. As is further known, the degree of stiffness of a medical device may be determined by the materials from which it is comprised, the shape and dimensions of the medical device, and any braiding utilized in its construction. The middle section 102 may comprise a round cross section having a diameter 112 that, in some embodiments, may be larger than the diameter 111 of the distal section 101 and the proximal section 103. The middle section 102 may include a tight diametral tolerance. In some embodiments, the diametral tolerance of the diameter 112 may be about ±0.002 inches, ±0.001 inches, ±0.0005 inches, ±0.0002 inches, or tighter.

The middle section 102 may comprise a distal transition portion 106. The distal transition portion 106 may define a smooth transition of physical properties between the distal section 101 and the middle section 102. The distal transition portion 106 may comprise a taper to transition the diameter 111 of the distal section 101 to the diameter 112 of the middle section 102. The distal transition portion 106 may also be constructed to transition the flexibility of the distal section 101 to the stiffness of the middle section 102. In some embodiments, the distal transition portion 106 may define a strain relief. In a similar fashion, the middle section 102 may comprise a proximal transition portion 107. The proximal transition portion 107 may define a smooth transition of physical properties between the proximal section 103 and the middle section 102. In some embodiments, the middle section 102 may be configured to be disposed within the vasculature of a patient. More specifically, the length of the middle section 102 may be sufficiently short to traverse curved portions of an intended vasculature.

Figure 2:
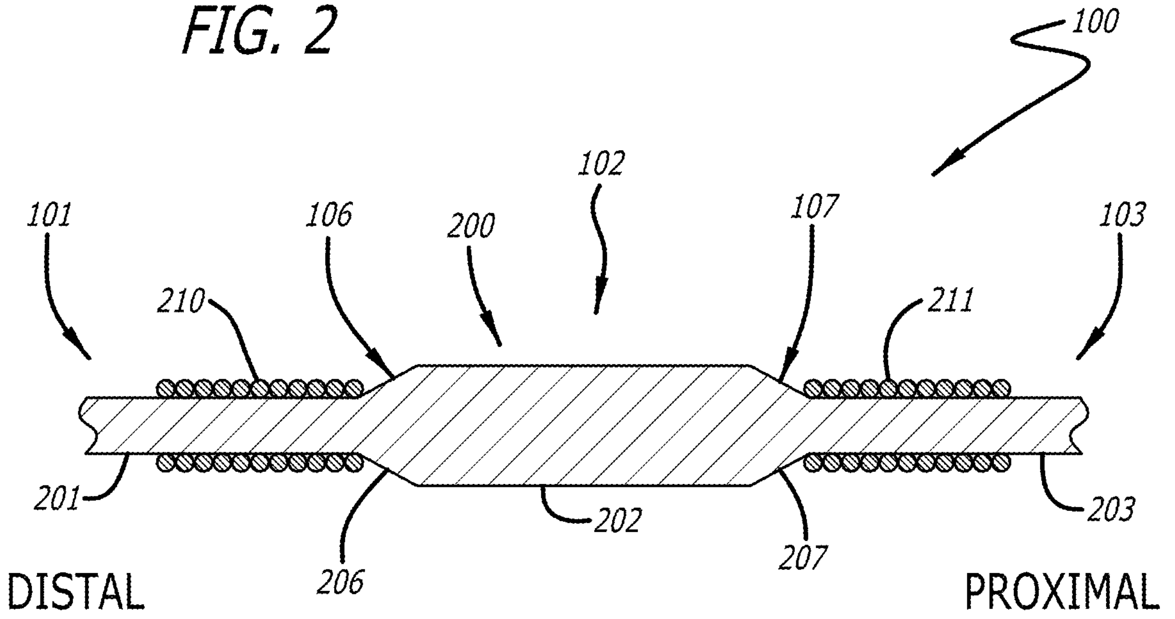
FIG. 2 is a cross-sectional side view of a portion of the needle tip blunting guidewire of FIG. 1 illustrating a first construction method of the needle tip blunting guidewire, in accordance with some embodiments.
Figure 3:
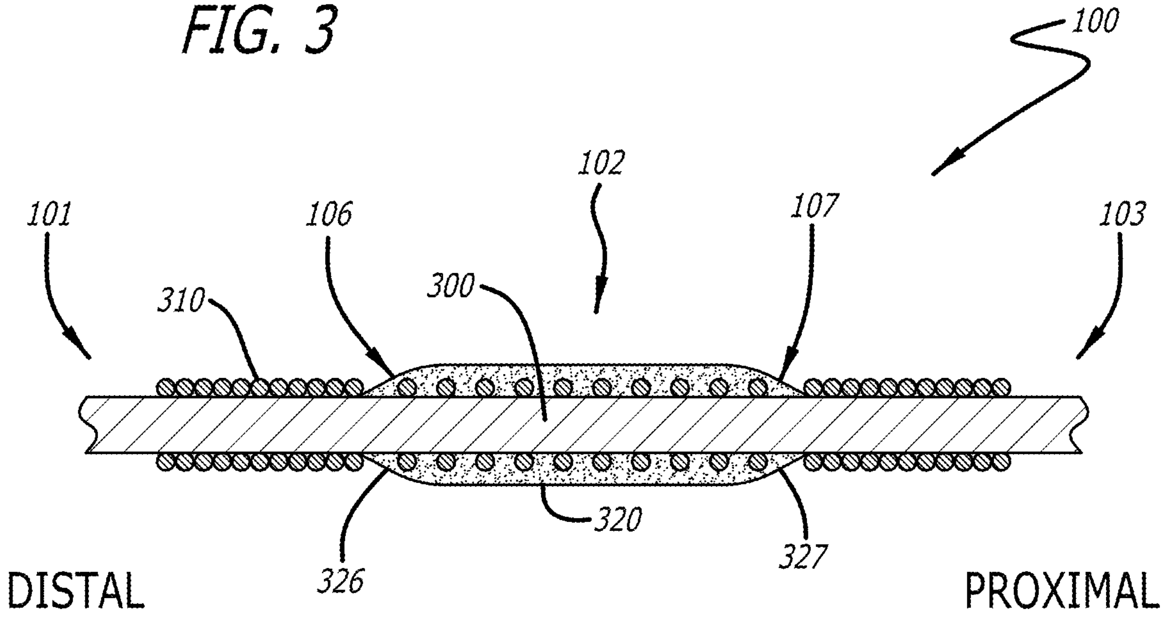
FIG. 3 is a cross-sectional side view of a portion of the needle tip blunting guidewire of FIG. 1 illustrating a second construction method of the needle tip blunting guidewire, in accordance with some embodiments.
Figure 4:
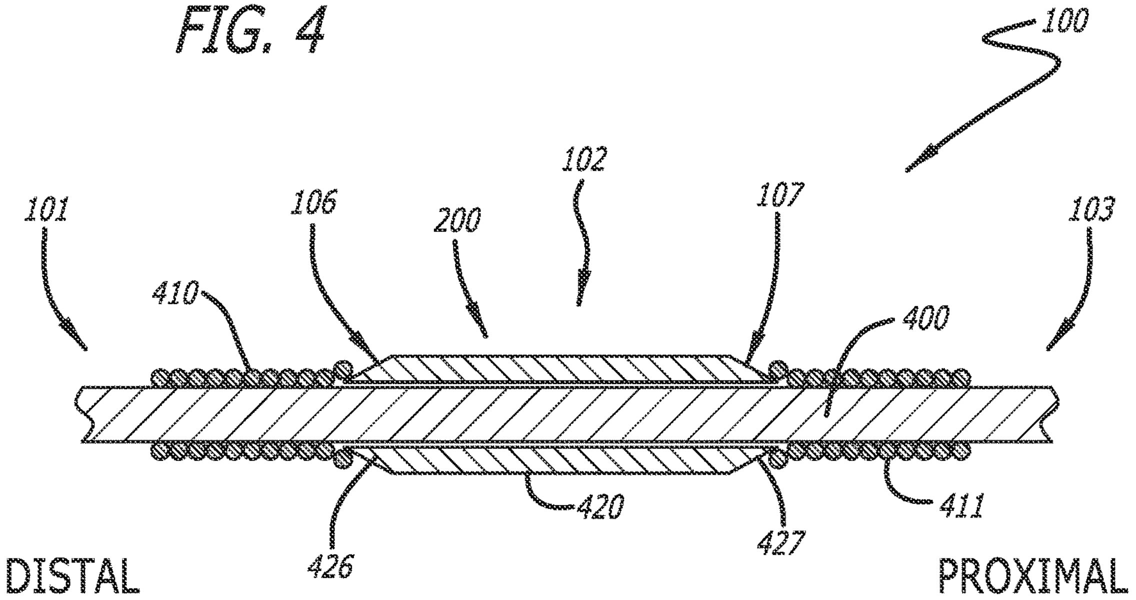
FIG. 4 is a cross-sectional side view of a portion of the needle tip blunting guidewire of FIG. 1 illustrating a third construction method of the needle tip blunting guidewire, in accordance with some embodiments.

FIGS. 2-4 illustrate different methods of constructing the NTBG 100. As shown in FIG. 2 according a first construction method, the NTBG 100 may be constructed of a wire 200 having a solid core. The wire 200 may extend the entire length of the NTBG 100. In some embodiments, the wire 200 may be formed of a nitinol material. In the embodiment of FIG. 2, the wire 200 includes a distal wire portion 201, a middle wire portion 202, and a proximal wire portion 203 that correspond with the distal, middle, and proximal sections 101, 102, 103, respectively. A diameter of the wire 200 may be sufficiently thin along the distal wire portion 201 and the proximal wire portion 203 to facilitate the flexibility of the distal and proximal sections 101, 103, respectively. The distal wire portion 201 and the proximal wire portion 203 may also be wrapped with the distal coil 210 and the proximal coil 211, respectively. A diameter of the wire 200 along the middle wire portion 202 may be sufficiently thick to facilitate the stiffness of the middle section 102. The middle wire portion 202 may define the diameter 112 of the middle section 102. The middle wire portion 202 may also be formed via a process consistent with defining the diametral tolerance of the middle section 102, such as grinding, for example. In some embodiments, the wire 200 may include a distal taper 206 to transition the diameter of the middle wire portion 202 to the diameter of the distal wire portion 201 which may at least partially define the transition portion 106. Similarly, the wire 200 may include a proximal taper 207 to transition the diameter of the middle wire portion 202 to the diameter of the proximal wire portion 201 which may at least partially define the transition portion 107.

FIG. 3 illustrates a second construction method of the NTBG 100. The second construction method of the NTBG 100 includes a wire 300 having a solid core extending the length of the NTBG 100. The wire 300 may be formed of nitinol. In some embodiments, a diameter of the wire may be constant along the length of the wire 300, and the wire 300 may be wrapped with a coil 310 along the length of the wire 300. The middle section 102 of the NTBG 100 is formed by applying a material 320 around the wire 300 and the coil 310 along a middle portion of the wire 300. The applied material 320 may be a potting or casting material such as an epoxy. In some embodiments, the material 320 may be a thermoplastic material that is insert molded onto the wire 300 and coil 310. The material 320 may fill in gaps between coils 310 which may alter the flexibility of the wire 300 and coil 310. The material 320 may add to the diameter of the coil 310 to define the diameter 112 of the middle section 102. The material 320 may be a liquid when applied and may transform into a solid after application. Once hardened, the material 320 may define the desired stiffness of the middle section 102. After hardening, the material 320 may be formed via a process consistent with defining the diametral tolerance of the of the diameter 112 of middle section 102, such as grinding, for example. The material 320 may include a distal taper 326 to transition the diameter of the middle section 102 to the diameter of the distal section 101 which may at least partially define the transition portion 106. Similarly, the material 320 may include a proximal taper 327 to transition the diameter of the middle portion 102 to the diameter of the proximal section 103 which may at least partially define the transition portion 107.

FIG. 4 illustrates a third construction method of the NTBG 100. The third construction method of the NTBG 100 includes a wire 400 having a solid core extending the length of the NTBG 100. The wire 400 may be formed of nitinol. In some embodiments, a diameter of the wire may be constant along the length of the wire 400. A cannula 420 may be threaded onto the wire 400 and attached to the wire 400. The wire 400 may be wrapped along the distal section 101 and the proximal section 103 with distal coil 410 and proximal coil 411, respectively. The middle section 102 of the NTBG 100 is defined by the cannula 420. The cannula portion 420 may be formed of a metal or a rigid plastic to define the desired stiffness of the middle section 102. The cannula 420 may also be formed of a process consistent with defining the diametral tolerance of the diameter 112 of the middle section 102, such as grinding, for example. The cannula 420 may include a distal taper 426 to transition the diameter of the middle section 102 to the diameter of the distal section 101 which may at least partially define the transition portion 106. Similarly, the cannula 420 may include a proximal taper 427 to transition the diameter of the middle section 102 to the diameter of the proximal section 103 which may at least partially define the transition portion 107.

Figure 5:
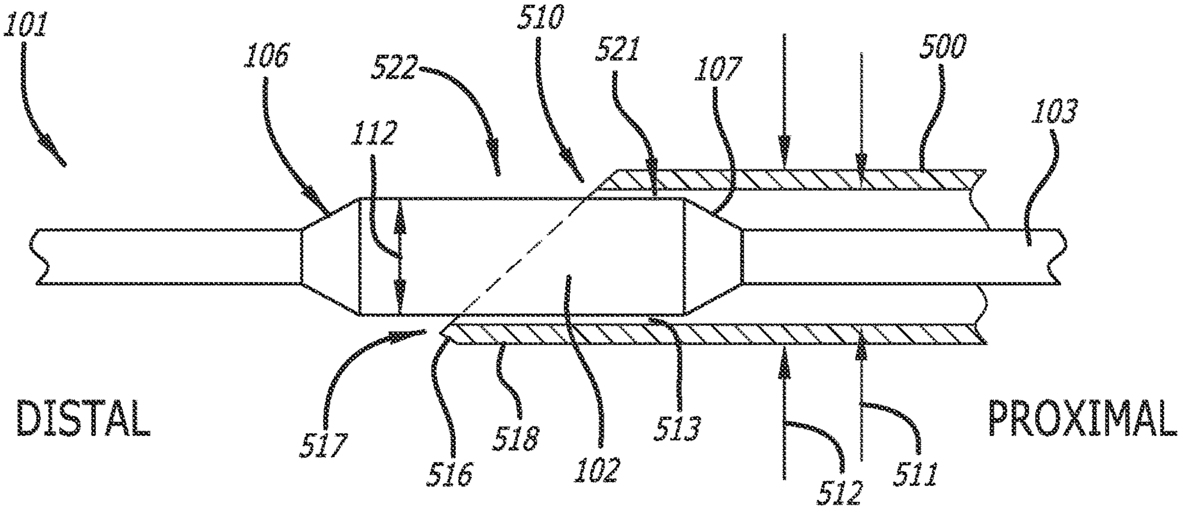
FIG. 5 is a cross-sectional side view of a portion of the needle tip blunting guidewire of FIG. 1 in combination with a portion of a cannula, in accordance with some embodiments.

FIG. 5 illustrates the NTBG 100 in use with a cannula 500. FIG. 5 shows a portion of the cannula 500 threaded onto the NTBG 100. In some embodiments, the NTBG 100 may be provided with a cannula 500. The cannula 500 includes an inside diameter 511 and an outside diameter 512. The cannula 500 is threaded onto the proximal section 103, so that a tip 510 of the cannula 500 is disposed along the middle section 102. The inside diameter 511 of the cannula 500 is sized to correspond with the diameter 112 of the middle section 102. More specifically, the inside diameter 511 and the diameter 112 are sized, so that a diametral clearance 513 between the cannula 500 and the middle section 102 is minimized while allowing longitudinal sliding motion of the cannula 500 with respect to the middle section 102. In some embodiments, the diametral clearance may be less than about 0.003 inches, 0.002 inches, 0.001 inches, 0.0005 inches, or less.

As shown in FIG. 5, the middle section 102 is positioned relative to the cannula 500, so that a proximal portion 521 of the middle section 102 is disposed within the cannula 500 and a distal portion 522 extends distally away from the tip 510 of the cannula 500. The proximal portion 521 may include a sufficient length, so that in combination with the clearance 513, the distal portion 522 is constrained to be parallel with the cannula 500. Lengths of the middle section 102, the proximal portion 521, and the distal portion 522 may be defined in relation to the diameter 112 of the middle section 102. In some embodiments, the length of the proximal portion 521 may be about 1, 2, 3, 4 or more times the diameter 112 of middle section 102. In some embodiments, the length of the distal portion 521 may be about 0.25, 0.5, 1, 2, or more times the diameter 112. In some embodiments, a length of the middle section 102 may be about 1.25, 1.5, 2, 3, 4 or more times the diameter 112.

The tip 510 of the cannula 500 may be a sharp tip such as a tip consistent with piercing skin and/or a vascular wall. In other embodiments, the tip 510 may be a configured insertion through a septum. In some embodiments, the tip 510 may include a sharp point 517 disposed on the outside surface 518 of the cannula 500. In other embodiments, the tip 510 may include a facet 516 that is cut to displace the point 517 inward away from the outside surface 518 of the cannula 500.

The NTBG 100 may be provided in multiple configurations. For example, in some embodiment configurations, the distal section 101 may include a length consistent with placement of an intravascular device. Similarly, configurations of NTBG 100 may be sized for use with specific cannula gauges. For example, an embodiment of the NTBG 100 may be configured for use with a variety of cannulas of a specified gauge. As may be appreciated by one of ordinary skill, configurations of NTBG 100 may be provided with any combination of physical properties for each of the distal, middle, and proximal sections (101, 102, 103), such as length, diameter, and flexibility.

Figure 6:
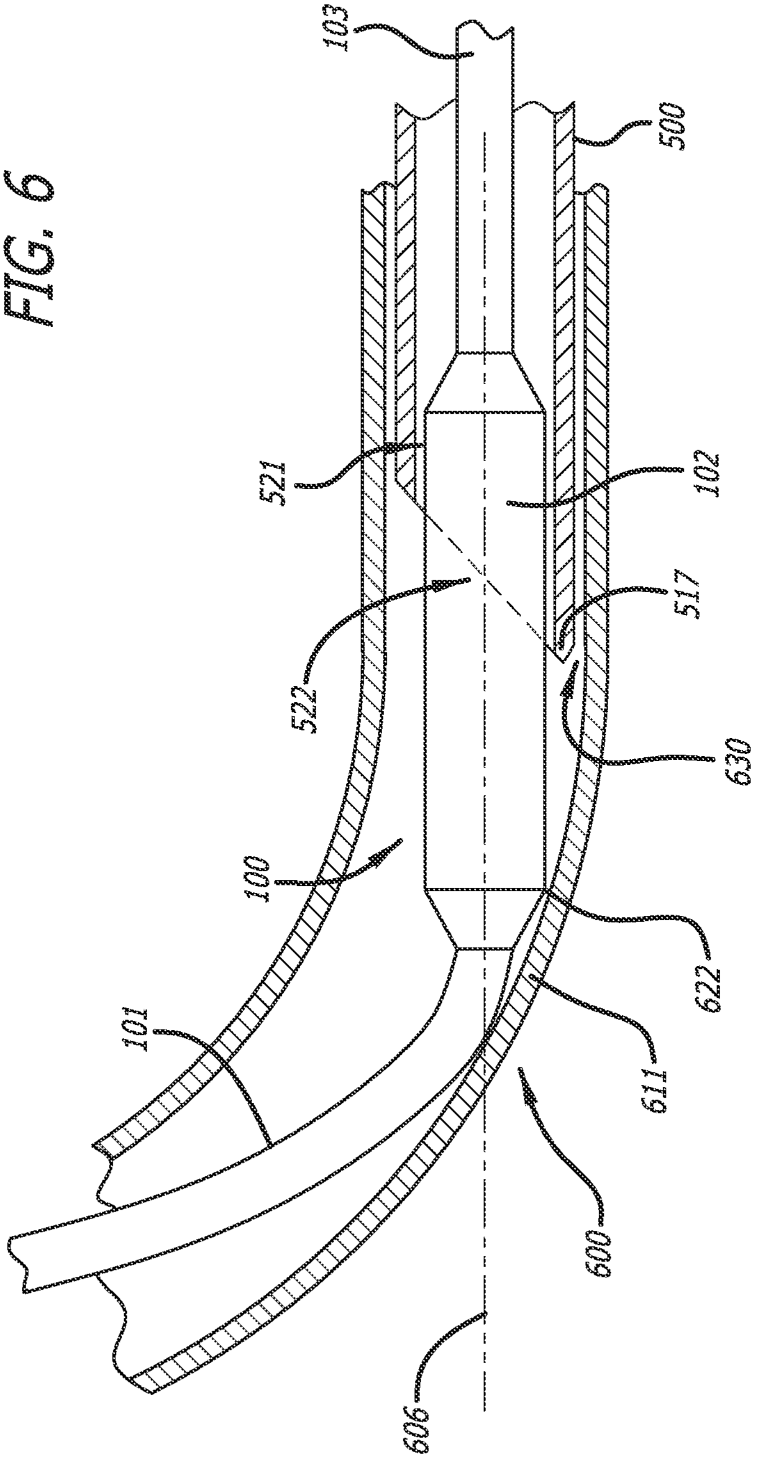
FIG. 6 is a cross-sectional side view of the combination of FIG. 5 in further combination with a portion of a tubular member, in accordance with some embodiments.

FIG. 6 illustrates the combination of the NTBG 100 and the cannula 500 of FIG. 5 in further use with a tubular member 600. In some embodiments, the tubular member 600 may be an intravascular catheter. As shown in FIG. 6, the longitudinal position of the middle section 102 with respect to the cannula 500 is the same as illustrated in FIG. 5. Also as described above with reference to FIG. 5, the distal portion 522 extends distally away from the tip 510 and is constrained to be parallel with the cannula 500. FIG. 6 illustrates the combination of FIG. 5 inserted into the tubular member 600. The NTBG 100 and the cannula 500 are inserted into the tubular member 600 so that the cannula tip 510 and the distal portion 522 of the middle section 102 are disposed within the tubular member 600. The tubular member 600 is shown in a curved state with the tubular member 600 curving away from a longitudinal axis 606 of the middle section 102.

FIG. 6 illustrates an instance, wherein the curve of the tubular member 600 is sufficiently sharp to cause a tubular wall 611 of the tubular member 600 to contact the distal portion 522 at a contact point 622. As the distal portion 522 is a stiff extension of the cannula 500, the contact between the tubular wall 611 and the distal portion 522 limits the sharpness of the curve along a section of the tubular member 600 extending between the contact point 622 and the cannula 500. Limiting the sharpness of the curve ensures a separation distance 630 between the point 517 of the cannula tip 510 and the tubular wall 611. The separation distance 630 in turn ensures that the point 517 does not contact or pierce the tubular wall 611. By way of summary, the distal portion 522 of the middle section 102 prevents the tip 510 of the cannula 500 from piercing the tubular member 600. In other words, the sharp tip 510 of the cannula 500 is converted into a blunt tip by the distal portion 522 of the middle section 102, protecting the tubular member 600 from being pierced by the point 517. Therefore, by first inserting the NTBG 100 into a cannula 500, a clinician may insert the cannula 500 into a tubular member 600 without concern for piercing the tubular member 600.

In some instances, the tubular member 600 may comprise flexibility and stiffness characteristics to cause a curvature of the tubular member 600 to extend proximally beyond the catheter tip 510 when the tubular wall 611 is in contact with the distal portion 522 at the contact point 622. In this instance, the curvature of the tubular member 600 may displace the tubular wall 611 radially away from the outside surface 518 of the cannula 500 which may at least partially define the separation distance 630. In such an instance, piercing of the tubular member 600 may be prevented in the event that the tip 517 is disposed on the outside surface 518 of the cannula 500.

Methods of use of the NTBG may include the following steps or processes. A method may include a step of inserting the NTBG through the cannula. The NTBG may be inserted distally, i.e., inserting the distal end first, or proximally, i.e., inserting the proximal end first. Threading the cannula onto the NTBG may be analogous to inserting the NTBG through the cannula. In some embodiments, the NTBG may be partially inserted so that the distal end or the proximal end of the NTBG is disposed within the cannula.

A method may include a step of positioning the middle section of the NTBG adjacent the cannula tip, so that the tip is disposed between the distal end and the proximal end of the middle section and, so that the distal portion may effectively blunt the sharp tip of the cannula.

A method may include a step of visually observing indicia disposed on the proximal section of the NTBG in relation to a proximal end of the cannula to determine the position of the middle section with respect to the cannula tip. In some instances, the cannula tip may not be visible to the clinician and therefore, the position of the middle section with respect to the cannula tip may not be observable. The location of an indicium with respect to the proximal end of the cannula may provide a visual indication to the clinician that the middle section is positioned adjacent the cannula tip.

A method may include a step of contacting the tubular member (catheter) with the middle section, i.e. the distal portion of the middle section, to constrain the tubular member away from the sharp point of the cannula. More specifically, the distal portion contacts an inside surface of the tubular wall of the tubular member, so that the sharp point of the cannula does not gouge or pierce the tubular wall.

A method may include a step of inserting the NTBG through a catheter. The NTBG may be inserted distally, i.e., inserting the distal section first, or proximally, i.e., inserting the proximal section first. Threading the catheter onto the NTBG may be analogous to inserting the NTBG through the catheter. In some embodiments, the NTBG may be partially inserted so that a distal end of the NTBG is disposed within the catheter. The NTBG may be inserted through the catheter before or after the catheter has been inserted into a patient.

A method may include a step of inserting the cannula and the NTBG through a catheter in a single step. This step may be performed after the NTBG is inserted through the cannula and after the middle section is positioned adjacent the cannula tip. During this step, the position of the NTBG with respect to the cannula may be constrained so that the middle section remains positioned adjacent the cannula tip.

A method may include a step of inserting the NTBG and the cannula through a catheter in a single step. This step may be performed after the NTBG is inserted through the cannula and after the middle section is positioned adjacent the cannula tip. During this step, the position of the NTBG with respect to the cannula may be constrained so that the middle section remains positioned adjacent the cannula tip.

A method may include a step of inserting the NTBG, the cannula, and the catheter through a second catheter in a single step. This step may be performed after the NTBG is inserted through the cannula, after the middle section is positioned adjacent the cannula tip, and after the NTBG and the cannula are inserted though the first catheter. During this step, the position of the NTBG with respect to the cannula may be constrained so that the middle section remains positioned adjacent the cannula tip.

A method may include a step of inserting the NTBG into the vasculature of the patient. In some embodiments, only the distal section of the NTBG is inserted into the patient. In other embodiments, the distal section and at least a portion of the middle section is inserted into the patient. Still in other embodiments, the distal section, the middle section and at least a portion of proximal section is inserted into the patient.

A method may include a step of removing the cannula from the catheter. In this step, the cannula is displaced proximally relative to the catheter until no portion of the cannula is inserted into the catheter. In some embodiments, the NTBG may remain inserted through the cannula.

A method may include a step of removing the cannula from the NTBG. Removing the cannula from the NTBG includes displacing the cannula proximally off the proximal end of the NTBG. In some embodiments, a catheter may remain threaded onto the NTBG.

A method may include a step of threading a catheter onto the NTBG in the absence of the cannula. In other words, the NTBG may be inserted into the patient and the catheter may be threaded onto the NTBG from the proximal end. The NTBG may serve as a guidewire as the catheter is inserted through the vasculature of the patient.

A method may include a step of visually observing indicia disposed on the proximal section of the NTBG in relation to the vascular insertion site. The location of an indicium with respect to the vascular insertion site may provide a visual indication to the clinician as to the position of the distal end of the NTBG along the vasculature of the patient.

While some particular embodiments have been disclosed herein, and while the particular embodiments have been disclosed in some detail, it is not the intention for the particular embodiments to limit the scope of the concepts provided herein. Additional adaptations and/or modifications can appear to those of ordinary skill in the art, and, in broader aspects, these adaptations and/or modifications are encompassed as well. Accordingly, departures may be made from the particular embodiments disclosed herein without departing from the scope of the concepts provided herein.

What is claimed is:

1. A method of using a guidewire, the method comprising:
- obtaining the guidewire, the guidewire comprising:
  - a distal section,
  - a proximal section, and
  - a middle section disposed between the distal section and the proximal section, wherein the middle section has a flexural stiffness that is greater than a flexural stiffness of both of the distal section and the proximal section;
- threading a cannula onto the guidewire, including inserting the distal section distally through the cannula from a proximal end of the cannula;
- positioning a tip of the cannula between a distal end and a proximal end of the middle section; and
- inserting the cannula and the guidewire distally through a tubular member while maintaining a position of the cannula with respect to the guidewire.

2. The method of claim 1, further comprising contacting the tubular member with the middle section to constrain the tubular member away from a sharp point of the cannula.

3. The method of claim 1, wherein after positioning the tip of the cannula, at least a portion of the proximal section is disposed within the cannula.

4. The method of claim 1, wherein the tubular member is a first intravascular catheter.

5. The method of claim 4, wherein the first intravascular catheter is at least partially inserted into a vasculature of a patient.

6. The method of claim 4, further comprising inserting the guidewire and the cannula into a second intravascular catheter.

7. The method of claim 6, further comprising inserting the first intravascular catheter into the second intravascular catheter.

8. The method of claim 1, further comprising inserting the distal section of the guidewire into a vasculature.

9. The method of claim 8, wherein inserting the distal section of the guidewire into the vasculature is performed before threading the cannula onto the guidewire.

* * * * *